US006068600A

United States Patent [19]

Johnson et al.

[11] Patent Number: 6,068,600

[45] Date of Patent: *May 30, 2000

[54] USE OF HOLLOW MICROCAPSULES

[75] Inventors: Richard Alan Johnson, Nottingham, United Kingdom; Paulus Antonius van der Wouw, Breukelen, Netherlands

[73] Assignee: Quadrant Healthcare (UK) Limited, Ruddington, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/761,600

[22] Filed: Dec. 6, 1996

[51] Int. Cl.$^7$ ...................................................... A61B 8/00
[52] U.S. Cl. .............................................................. 600/458
[58] Field of Search ................................... 600/458, 437, 600/442; 424/9.3, 9.5, 9.52, 9.51, 489, 491

[56] References Cited

U.S. PATENT DOCUMENTS

| | | | |
|---|---|---|---|
| 2,797,201 | 6/1957 | Veatch et al. | 260/2.5 |
| 3,501,419 | 3/1970 | Bridgeford | 260/2.5 |
| 3,781,230 | 12/1973 | Vassilaiades et al. | 260/2.5 B |
| 3,937,668 | 2/1976 | Zolle | 252/316 |
| 4,089,800 | 5/1978 | Temple | 252/316 |
| 4,102,806 | 7/1978 | Kondo et al. | 252/316 |
| 4,107,288 | 8/1978 | Oppenheim et al. | 424/22 |
| 4,127,622 | 11/1978 | Watanabe et al. | 264/13 |
| 4,147,767 | 4/1979 | Yapel | 424/22 |
| 4,173,488 | 11/1979 | Vassiliades et al. | 106/213 |
| 4,247,406 | 1/1981 | Widder et al. | 252/62.53 |
| 4,276,885 | 7/1981 | Tickner et al. | 128/660 |
| 4,316,391 | 2/1982 | Tickner | 73/861.25 |
| 4,349,530 | 9/1982 | Royer | 424/19 |
| 4,357,259 | 11/1982 | Senyei et al. | 252/316 |
| 4,420,442 | 12/1983 | Sands | 264/13 |
| 4,442,843 | 4/1984 | Rasor et al. | 128/660 |
| 4,466,442 | 8/1984 | Hilmann et al. | 128/653 |
| 4,718,433 | 1/1988 | Feinstein | 128/660 |
| 4,774,958 | 10/1988 | Feinstein | 128/660.01 |
| 4,808,408 | 2/1989 | Baker et al. | 424/408 |
| 4,844,882 | 7/1989 | Widder et al. | 424/9 |
| 4,900,540 | 2/1990 | Ryan et al. | 424/9 |
| 4,957,656 | 9/1990 | Cerny et al. | 252/311 |
| 4,960,351 | 10/1990 | Kendall, Jr. et al. | 425/6 |
| 4,968,562 | 11/1990 | Delgado | 428/402 |
| 4,981,625 | 1/1991 | Rhim et al. | 264/13 |
| 5,137,928 | 8/1992 | Erbel et al. | 521/56 |
| 5,141,738 | 8/1992 | Rasor et al. | 424/2 |
| 5,147,631 | 9/1992 | Glajch et al. | 424/9 |

(List continued on next page.)

FOREIGN PATENT DOCUMENTS

| | | |
|---|---|---|
| 80297/91 | 1/1992 | Australia . |
| 2036107 | 8/1991 | Canada . |
| 1336164 | 7/1995 | Canada . |
| 0 052 575 | 5/1982 | European Pat. Off. . |
| 0 091 555 | 10/1983 | European Pat. Off. . |
| 0 131 540 | 1/1985 | European Pat. Off. . |
| 0 202 017 | 11/1986 | European Pat. Off. . |
| 0 224 934 | 6/1987 | European Pat. Off. . |
| 0 324 938 | 7/1989 | European Pat. Off. . |
| 0 327 490 | 8/1989 | European Pat. Off. . |
| 0 381 543 | 8/1990 | European Pat. Off. . |
| 0 398 935 | 11/1990 | European Pat. Off. . |
| 0 458 079 | 11/1991 | European Pat. Off. . |
| 0 458 745 | 11/1991 | European Pat. Off. . |
| 0 494 615 | 7/1992 | European Pat. Off. . |
| 0 554 213 | 8/1993 | European Pat. Off. . |
| 0 606 486 | 7/1994 | European Pat. Off. . |
| 0 611 567 | 8/1994 | European Pat. Off. . |
| 2 660 864 | 10/1991 | France . |

(List continued on next page.)

OTHER PUBLICATIONS

Miller, D. L., "Ultrasonic detection of resonant cavitation bubbles in a flow tube by their second–harmonic emissions," *Ultrasonics* 19(5):217–224 (1981).

de Jong, N. et al., "A Computerized System That Uses High–Frequency Data for Analysis of Myocardial Contrast Echocardiograms," *J. Am. Soc. Echocardiography* 3(2):99–105 (1990).

de Jong, N. et al., "Principles and recent developments in ultrasound contrast agents," *Ultrasonics* 29:324–330 (1991).

de Jong, N. et al., "Absorption and scatter of encapsulated gas filled microspheres: theoretical considerations and some measurements," *Ultrasonics* 30(2):95–103 (1992).

English language abstract for WO 93/25242 (Document AM9), Orbit File WPAT (Derwent World Patent Index).

English language translation for WO 95/07072 (Document A09).

Aldrich, J.E. & Johnston, J.R., "Use of the Spinning Disk Technique to Produce Monodisperse Microspheres of Human Serum Albumin for Labelling with Radioisotopes," *Int. J. Appl. Rad. Isot.* 25:15–18 (1974).

Barnhart, J. et al., "Characteristics of Albunex: Air–Filled Albumin Microspheres for Echocardiography Contrast Enhancement," *Invest. Radiol.* 25:S162–S164 (1990).

Basu, S. & Bhattacharya, G., "Some Aspects of the Phenomenon of Coacervation," *Science* 115:544–545 (1952).

Baveja, S. K. et al., "Microencapsulation of soluble pharmaceuticals," *J. Microencapsulation* 3(1):33–37 (1986).

Beller, G. A. et al., "Assessment of Regional Myocardial Perfusion by Positron Emission Tomography after Intracoronary Administration of Gallium–68 Labeled Albumin Microspheres," *J. Computer Assisted Tomography* 3(4):447–452 (1979).

(List continued on next page.)

*Primary Examiner*—George Manuel
*Attorney, Agent, or Firm*—Sterne, Kessler, Goldstein & Fox P.L.L.C.

[57] ABSTRACT

A method of generating an ultrasound image comprising the steps of (i) introducing into the location to be imaged an ultrasound contrast agent obtained by spraying a solution or suspension of a wall forming material into a heated gas to form hollow microcapsules, (ii) exposing the microcapsules to ultrasound energy at an insonation frequency of less than 3.5 MHz and (iii) creating an image based on the scattering of the ultrasound energy by the microcapsules.

12 Claims, No Drawings

U.S. PATENT DOCUMENTS

| | | | |
|---|---|---|---|
| 5,190,982 | 3/1993 | Erbel et al. | 521/56 |
| 5,196,183 | 3/1993 | Yudelson et al. | 424/9 |
| 5,205,287 | 4/1993 | Erbel et al. | 128/632 |
| 5,215,680 | 6/1993 | D'Arrigo | 252/307 |
| 5,271,928 | 12/1993 | Schneider et al. | 424/9 |
| 5,271,961 | 12/1993 | Mathiowitz et al. | 427/213.31 |
| 5,370,861 | 12/1994 | Klaveness et al. | 424/5 |
| 5,380,519 | 1/1995 | Schneider et al. | 424/9 |
| 5,410,516 | 4/1995 | Uhlendorf et al. | 367/7 |
| 5,425,366 | 6/1995 | Reinhardt et al. | 128/662.02 |
| 5,498,421 | 3/1996 | Grinstaff et al. | 424/450 |
| 5,501,863 | 3/1996 | Rössling et al. | 424/489 |
| 5,518,709 | 5/1996 | Sutton et al. | 424/9.52 |
| 5,536,490 | 7/1996 | Klaveness et al. | 424/9.52 |
| 5,543,162 | 8/1996 | Timonen et al. | 426/89 |
| 5,547,656 | 8/1996 | Unger | 424/9.4 |
| 5,567,413 | 10/1996 | Klaveness et al. | 424/9.51 |
| 5,567,414 | 10/1996 | Schneider et al. | 424/9.52 |
| 5,605,673 | 2/1997 | Schutt et al. | 424/9.51 |
| 5,643,553 | 7/1997 | Schneider et al. | 424/9.52 |
| 5,658,551 | 8/1997 | Schneider et al. | 424/9.51 |
| 5,674,468 | 10/1997 | Klaveness et al. | 424/9.3 |
| 5,676,925 | 10/1997 | Klaveness et al. | 424/9.3 |
| 5,695,741 | 12/1997 | Schutt et al. | 424/9.52 |
| 5,741,478 | 4/1998 | Osborne et al. | 424/9.52 |

FOREIGN PATENT DOCUMENTS

| | | |
|---|---|---|
| 56-129035 | 10/1981 | Japan . |
| 4-145131 | 5/1992 | Japan . |
| 4-506931 | 12/1992 | Japan . |
| 6-507884 | 9/1994 | Japan . |
| 227 869 | 11/1992 | New Zealand . |
| 89 0873 | 2/1989 | South Africa . |
| 1 288 583 | 9/1972 | United Kingdom . |
| WO 84/02838 | 8/1984 | WIPO . |
| WO 90/13780 | 11/1990 | WIPO . |
| WO 91/01706 | 2/1991 | WIPO . |
| WO 91/06286 | 5/1991 | WIPO . |
| WO 91/09629 | 7/1991 | WIPO . |
| WO 91/12823 | 9/1991 | WIPO . |
| WO 91/15244 | 10/1991 | WIPO . |
| WO 91/16080 | 10/1991 | WIPO . |
| WO 92/05806 | 4/1992 | WIPO . |
| WO 92/17212 | 10/1992 | WIPO . |
| WO 92/17213 | 10/1992 | WIPO . |
| WO 92/18164 | 10/1992 | WIPO . |
| WO 93/02712 | 2/1993 | WIPO . |
| WO 93/25242 | 12/1993 | WIPO . |
| WO 94/08627 | 4/1994 | WIPO . |
| WO 95/07072 | 3/1995 | WIPO . |
| WO 96/15814 | 5/1996 | WIPO . |
| WO 96/18388 | 6/1996 | WIPO . |

OTHER PUBLICATIONS

Buchanan, J.W. et al., "Labelling Albumin Microspheres with $^{113m}$In," *J. Nucl. Med.* 10(7):487–490 (1969).

Cheng, K. T. et al., "The Production and Evaluation of Contrast–Carrying Liposomes Made with an Automatic High–Pressure System," *Investigative Radiol.* 22(1):47–55 (1987).

Clausen, G. et al., "Distribution of blood flow in the dog kidney. III. Local uptake of 10 μm and 15 μm microspheres during renal vasodilation and constriction," *Acta Physiol. Scand.* 113:471–479 (1981).

Conte, U. et al., "Spray Dried Albumin Microspheres Containing Nicardipine," *Eur. J. Pharm. Biopharm.* 40(4):203–208 (1994).

Cremers, H. F. M. et al., "Albumin–Heparin Microspheres As Carriers for Cytostatic Agents," *J. Controlled Release* 11:167–179 (1990).

Davis, S. S. and L. Illum, "Microspheres As Drug Carriers," *Drug Carrier Systems,* F. H. D. Roerdink and A. M. Kroon, eds., New York: John Wiley & Sons, Ltd., pp. 131–153 (1989).

Deasy, P.B., "Coacervation—Phase Separation Procedures Using Aqueous Vehicles," in: *Microencapsulation and Related Drug Processes,* New York: Marcel Dekker, Inc., pp. 61–69 (1984).

Durand–Keklikian, L. and Partch, R. E., "Microencapsulation of Oil Droplets by Aerosol Techniques —I. Metal Oxide Coatings," *J. Aerosol Sci.* 19(4):511–521 (1988).

Ellison, J.M., "Adaptation of the Spinning Top Generator to Provide Aerosols in the Respirable Range," *Ann. Occup. Hyg.* 10:363–367 (1967).

Feinstein, S.B. et al., "Microbubble Dynamics Visualized in the Intact Capillary Circulation," *JACC* 4(3):595–600 (1984).

Galyean, R.D. & Cotterill, O.J., "Chromatography and Electrophoresis of Native and Spray–Dried Egg White," *J. Food Sci.* 44:1345–1349 (1979).

Grinstaff, M.W. & Suslick, K.S., "Air–filled proteinaceous microbubbles: Synthesis of an echo–contrast agent," *Proc. Natl. Acad. Sci. USA* 88:7708–7710 (1991).

Gupta, P.K. & Hung, C.T., "Albumin microspheres I: physico–chemical characteristics," *J. Microencapsulation* 6(4):427–462 (1989).

Haghpanah, M. et al.,"Drug delivery to the lung using albumin microparticles," 131st British Pharmaceutical Conference, London, England, *J. Pharm. Pharmacol.* 46(Suppl. 2):1138 (1994).

Heiler, J., "Controlled release of biologically active compounds from bioerodible polymers," *Biomaterials* 1:51–57 (1980).

ICI Promotional Leaflet, "Formulations with Spindrift," (Publication Date Unknown).

Kawashima, Y. et al., "Preparation of multiple unit hollow microspheres (microballoons) with acrylic resin containing tranilast and their drug release characteristics (in vitro) and floating behavior (in vivo)," *J. Controlled Release* 16:279–290 (1991).

Kondo, A., in: *Microcapsule Processing and Technology,* Van Valkenburg, J.W. (ed.), New York: Marcel Dekker, Inc., pp. 18–20, 61, 68, 70, 90–92, 106–109, 118–119 (1980).

Kramer, P.A., "Albumin Microspheres as Vehicles for Achieving Specificity in Drug Delivery," *J. Pharm. Sci.* 63(10):1646–1647 (1974).

Kwok, K. K. et al., "Production of 5–15 μm Diameter Alginate–Polylysine Microcapsules by an Air–Atomization Technique," *Pharm. Res.* 8(3):341–344 (1991).

Levy, M.–C. and Andry, M.–C., "Mixed–walled microcapsules made of cross–linked proteins and polysaccharides: preparation and properties," *J. Microencapsulation* 8(3):335–347 (1991).

McArdle, C. S. et al., "Cytotoxic–loaded Albumin microspheres: a novel approach to regional chemotherapy," *Br. J. Surg.* 75:132–134 (1988).

Modler, H.W. & Emmons, D.B., "Calcium as an Adjuvant for Spray–Drying Acid Whey," *J. Dairy Sci.* 61:294–299 (1978).

Morris, N.J. & Warburton, B., "Three–ply walled w/o/w microcapsules formed by a multiple emulsion technique," *J. Pharm. Pharmacol.* 34:475–479 (1982).

Morris, N. J. & Warburton, B., "Particle size analysis of microcapsules," *J. Pharm. Pharmacol.* 36:73–76 (1984).

Omotosho, J.A. et al., "The nature of the oil phase and the release of solutes from multiple (w/o/w) emulsions," *J. Pharm. Pharmacol.* 38:865–870 (1986).

Ophir, J. et al., "Aqueous Solutions as Potential Ultrasonic Contrast Agents," *Ultrasonic Imaging* 1(3):265–279 (1979).

Ophir, J. et al., "Ultrasonic Backscatter from Contrast Producing Collagen Microspheres," *Ultrasonic Imaging* 2:67–77 (1980).

Pande, S. et al., "Preparation, characterization and performance evaluation of neomycin–HSA microspheres," *J. Microencapsulation* 7(2):155–165 (1990).

Parkinson, T.L., "Effects of Spray–drying and Freezing on the Proteins of Liquid Whole Egg," *J. Sci. Fd Agric.* 26:1625–1637 (1975).

Porter, C. J. H., "The polyoxyethylene/polyoxypropylene block co–polymer Poloxamer–407 selectively redirects intravenously injected microspheres to sinusoidal endothelial cells of rabbit bone marrow," *FEBS Lett* 305(1):62–66 (1992).

Pryzborowski, M. et al., "Preparation of HSA Microspheres in a One–Step Thermal Denaturation of Protein Aerosol Carried in Gas–Medium," *Eur. J. Nucl. Med.* 7:71–72 (1982).

Raju, A. et al., "Human Serum Albumin Microspheres for Lung Imaging—Preparation and Evaluation," *Isotopenpraxis* 14:57–61 (1978).

Rettenmaier, M.A. et al., "In Vivo Alteration of RES Phagocytosis by Magnetic Albumin Microspheres," *J. Clin. Lab. Immunol.* 17:99–103 (1985).

Rosenberg, M. et al., "Factors Affecting Retention in Spray–Drying Microencapsulation of Volatile Materials," *J. Agric. Food Chem.* 38:1288–1294 (1990).

Sato, T. et al., "Porous Biodegradable Microspheres for Controlled Drug Delivery. I. Assessment of Processing Conditions and Solvent Removal Techniques," *Pharm. Res.* 5(1):21–30 (1988).

Scheffel, U. et al., "Albumin Microspheres for Study of the Reticuloendothelial System," *J. Nucl. Med.* 13:498–503 (1972).

Schlief, R., "Ultrasound contrast agents," *Curr. Opin. Radiol.* 3:198–207 (1991).

Schneider, M. et al., "Polymeric Microballoons as Ultrasound Contrast Agents: Physical and Ultrasonic Properties Compared with Sonicated Albumin," *Invest. Radiol.* 27:134–139 (1992).

Schroeder, H.G. et al., "Distribution of Radiolabeled Subvisible Microspheres after Intravenous Administration to Beagle Dogs," *J. Pharm. Sci.* 67(4):504–507 (1978).

Shah, M.V. et al., "An evaluation of albumin microcapsules prepared using a multiple emulsion technique," *J. Microencapsulation* 4(3):223–238 (1987).

Shapiro, J.R. et al., "Intravenous Contrast Echocardiography With Use of Sonicated Albumin in Humans: Systolic Disappearance of Left Ventricular Contrast After Transpulmonary Transmission," *JACC* 16(7):1603–1607 (1990).

Takenaka, H. et al., "Preparation of Enteric–Coated Microcapsules for Tableting by Spray–Drying Technique and In Vitro Simulation of Drug Release from the Tablet in GI Tract," *J. Pharm. Sci.* 69(1):1388–1392 (1980).

Takenaka, H. et al., "Mechanical Properties, Dissolution Behavior and Stability to Oxidation of L–Ascorbylmonostearate Microcapsules prepared by a Spray–Drying Polycondensation Technique," *Chem. Pharm. Bull.* 30(6):2189–2195 (1982).

Violante, M. R. et al., "Biodistribution of a Particulate Hepatolienographic CT Contrast Agent: A Study of Iodopamide Ethyl Ester in the Rat," *Investigative Radiol.* 16(1):40–45 (1981).

Wheatley, M.A. et al., "Contrast agents for diagnostic ultrasound: development and evaluation of polymer–coated microbubbles," *Biomaterials* 11:713–717 (1990).

White, C. et al., "Biodistribution and Clearance of Contrast–Carrying MREV Liposomes," *Investigative Radiol.* 25(10):1125–1129 (1990).

Widder, K.J. et al., "Magnetically Responsive Microspheres and Other Carriers for the Biophysical Targeting of Antitumor Agents," *Adv. Pharmacol. Chemother.* 16:213–271 (1979).

Wilkins, D. J. and Myers, P. A., "Studies on the Relationship Between the Electrophoretic Properties of Colloids and Their Blood Clearance and Organ Distribution in the Rat," pp. 568–576.

Zhang, D. et al., "Histochemical studies on the mechanism of macromolecule leakage across the glomerular capillary wall," *Histochem.* 96:115–121 (1991).

Abstract of EP 0 131 540 (Document AP1), WPI Account No. 85–020020/04, Derwent World Patents Index.

Abstract of EP 0 327 490 (Document AP2), WPI Account No. 89–229495/32, Derwent World Patents Index.

Abstract of EP 0 458 079 (Document AM4), WPI Account No. 91–347827/48, Derwent World Patents Index.

Abstract of EP 0 494 615 (Document AP4), WPI Account No. 92–235686/29, Derwent World Patents Index.

English translation of EP 0 494 615 (Document AP4).

English Language Translation of Japanese Patent No. 56–129035 (Document AO6).

English Language Abstract of Japanese Patent No. 56–129035 (Document AO6), Patent Abstracts of Japan (JPO and Japio, 1981).

English Language Abstract of Japanese Patent No. 04–145131 (Document AP6), Patent Abstracts of Japan (JPO and Japio, 1992).

USE OF HOLLOW MICROCAPSULES

FIELD OF THE INVENTION

The present invention relates to the use of hollow microcapsules in ultrasound imaging.

PRIOR ART

The evaluation of tissue perfusion is a major challenge to all ultrasonographers trying to determine the viability of human tissue.

To date there are no commercially available echocontrast agents that are capable of generating B Mode grey scale images of perfusion in the major organs of the body.

For example, echocardiographers currently rely on wall motion abnormalities at rest and during stress to determine the perfusion properties of the myocardium during ultrasound examination. Definitive studies to determine the perfusion status of the heart require the use of nuclear imaging techniques.

To achieve perfusion images during ultrasonographic examination of the organ of interest requires the practitioner to obtain clear images with an even baseline across the tissue. In several patients however, it has proved impossible to generate suitable pre-contrast (baseline) images without using low frequency ultrasound transducers.

The above problem is exacerbated during echocardiographic examinations since patients may present with conditions such as obesity or emphysema. Both of these factors can reduce the quality of the baseline image obtained. However, the baseline image can be improved by using lower frequency transducers since greater penetration can be achieved through tissue. Low insonation frequencies permit deep penetration to internal organs such as the heart whereas high insonation frequencies of 3.5 MHz or more afford poor penetration so that only peripheral imaging, of for example superficial blood vessels, is possible. A major problem associated with the use of low frequency transducers currently is that commercially available contrast agents, for example Albunex® (MBI, San Diego, USA), Levovist® (Schering AG, Berlin, Germany), or those in development show significantly reduced echocontrast images at lower transducer frequencies. As a result, it is not possible to reliably generate B Mode grey scale myocardial perfusion images at low transducer frequencies.

Ultrasound contrast agents can be introduced into the body to reflect or absorb ultrasound energy, or to resonate when exposed to such energy, and thereby provide an enhanced image of a part of the body. Examples of such contrast agents, in the form of hollow microcapsules, are given in Japanese patent application nos. 508032/1992 and 509745/1994 and in PCT/GB95/02673 (WO 96/15814). Such agents are injected into the patient's bloodstream and then the patient is subjected to ultrasound radiation.

SUMMARY OF THE INVENTION

During recent clinical studies with microcapsules of the said three patents a range of ultrasound machines/probes were used for contrast (fundamental) imaging. In each study a single injection of the microcapsules was administered during continuous insonation from the ultrasound machine. In machines where two different ultrasound probes were available it was discovered that at similar image settings (ie power, focus, etc) significantly better images were obtained with the lower frequency transducer.

During further pre-clinical and clinical studies harmonic imaging has been performed with the Advanced Technology Laboratories (ATL) HDI 3000 ultrasound machine. The machine is fitted with two ultrasound probes that are suitable for echocontrast imaging.

The lower frequency probe (P3-2) was found to give significantly better perfusion images with the microcapsules than the higher frequency probe (P5-3). As mentioned above, with other known contrast agents it has been reported that higher frequency ultrasound probes generated better harmonic images. We have now found that if the microcapsules of the said three patent applications are exposed to ultrasound at lower transducer frequencies, unpredictably improved imaging performance can be obtained.

Accordingly, a first aspect of the invention provides a method of generating an ultrasound image comprising the steps of (i) introducing into the location to be imaged an ultrasound contrast agent obtained by spraying a solution or suspension of a wall forming material into a heated gas to form hollow microcapsules, (ii) exposing the microcapsules to ultrasound energy at an insonation frequency of less than 3.5 MHz and (iii) creating an image based on the scattering of the ultrasound energy by the microcapsules.

In a second aspect, the invention provides a method of generating an ultrasound image comprising the steps of (i) introducing into the location to be imaged an ultrasound contrast agent obtained by spraying a solution or suspension of a wall forming material into a heated gas to form hollow microcapsules, (ii) exposing the microcapsules to ultrasound energy, the insonation frequency being varied below 3.5 MHz to identify and use a frequency at which the ultrasound is scattered optimally by the microcapsules, and (iii) creating an image based on the scattering of the ultrasound energy caused by the microcapsules.

The microcapsules of the invention generate improved echocontrast images when insonated with lower frequencies of ultrasound. In comparative studies using constant image settings, lower frequencies generated more consistent, brighter (more echoreflective) images of perfusion following administration of the microcapsules. At the high insonation frequencies ie. 3.5 MHz or more recommended for imaging with known ultrasound contrast agents poorer images are obtained with the microcapsules of the invention.

In human clinical studies, insonating frequencies below 3.5 MHz generate excellent perfusion images following administration of the microcapsules. Reducing the frequency of the probe enhances the image further. Below 3 MHz and preferably below 2.25 MHz insonation frequency the image is improved still further and such very low insonation frequencies constitute a preferred embodiment of the invention.

In vitro studies have shown that insonation at from 2.0 to 1.0 MHz also generates excellent echocontrast images with the microcapsules of the invention. Insonation at approximately 1.8 MHz and 1.0 MHz are still further preferred embodiments of the invention.

Improved imaging can be provided according to the first or second aspects of the invention when the ultrasound energy in step (ii) is at a high acoustic power.

At a certain threshold intensity of ultrasound energy, the amount of scattering from the microspheres suddenly increases, relative to the scattering from the other materials. Hence, the contrast may be enhanced.

Typically, this effect is seen at intensities above 100 kPa, especially at 400–500 kPa, whereas prior art techniques used intensities less than 100 kPa. Still higher intensities can lead to still further benefits; at intensities of over 1.0 MPa, preferably over 2.0 MPa, the enhanced scattering effect is coupled to an enhanced harmonic signal. An intensity of over 10.0 MPa is unlikely to be practicable for diagnostic purposes.

In an imaging process of the present invention, the intensity is commonly varied in order to detect the threshold referred to above. The intensity may be successively halved, starting from a high value, until the relative scattering changes. The video densitometry should be performed on a linear, rather than logarithmic, scale. If the still higher (eg 2.0 MPa) intensities are used, then the imaging equipment may be switched to detect harmonics.

At the low ultrasound frequencies of the invention the dose of microcapsules required to achieve images is extremely low. For example, a microcapsule dose of less than 50 μl of a $1.5 \times 10^9$ microcapsules per ml suspension in a 75 kg man is required when used in conjunction with harmonic imaging techniques.

DESCRIPTION OF PREFERRED (NON-LIMITING) EMBODIMENTS

The microcapsules may be made by the method of JP 508032/1992 (WO 92/18164), or by the method of JP 509745/1994 (WO 94/08627) or by the method of WO 96/15814, all of which are incorporated herein by reference. More specifically, any of the wall forming materials and additives disclosed in those documents may be used, any of the sizes of microcapsules disclosed in those documents may be used and the microcapsules may be used to image any of the locations disclosed in those documents.

Hence (referring to WO 94/08627), the microcapsules may be relatively large hollow microspheres of, for example, 10–20 μm, 12–25 μm or 15–20 μm diameter, (ii) hollow microspheres having a prolonged half-life in the human bloodstream or (iii) hollow microspheres which are adapted for selective targeting to an area of the human or animal body. These three microsphere products will be termed herein "the large microspheres", "the long life microspheres" and "the targeted microspheres", respectively.

The "long life microspheres" and "the targeted microspheres" may, if one wishes, consist of microspheres having a diameter of 0.05 to 50.0 μm (measured in the same way as the intermediate microspheres), but ranges of 0.1 to 20.0 μm and especially 1.0 to 8.0 μm are obtainable with the process of the invention and are preferred for echocardiography. One needs to take into account the fact that the second step may alter the size of the microspheres in determining the size produced in the first step.

The large, long life or targeted hollow microspheres may be such that more than 30%, preferably more than 40%, 50%, or 60%, of the microspheres have a diameter within a 2 μm range and, in the case of the long life or targeted microspheres, at least 90%, preferably at least 95% or 99%, have a diameter within the range 1.0–8.0 μm. In the case of the large microspheres, the corresponding diameter range is 12–25 μm.

Thus, the interquartile range may be 2 μm, with a median diameter (for the long life or targeted microspheres) of 3.5, 4.0, 4.5, 5.0, 5.5, 6.0 or 6.5 μm.

Thus, at least 30%, 40%, 50% or 60% of the long life or targeted microspheres may have diameters within the range 1.5–3.5 μm, 2.0–4.0 μm, 3.0–5.0 μm, 4.0–6.0 μm, 5.0–7.0 μm or 6.0–8.0 μm. Preferably a said percentage of the said microspheres have diameters within a 1.0 μm range, such as 1.5–2.5 μm, 2.0–3.0 μm, 3.0–4.0 μm, 4.0–5.0 μm, 5.0–6.0 μm, 6.0–7.0 μm or 7.0–8.0 μm.

The large, long life or targeted hollow microspheres may have proteinaceous walls in which at least 90%, preferably at least 95% or 99%, of the microspheres have a diameter in the range 1.0–8.0 μm (or, in the case of the large microspheres, 12–25 μm); at least 90%, preferably at least 95% or 99%, of the microspheres have a wall thickness of 40–500 nm, preferably 100–500 nm; and at least 50% of the protein in the walls of the microspheres is cross-linked.

Scanning electron microscopy of the microcapsules shows that they are hollow spheres with no solid matter other than in the wall. Hence, the wall thickness can either be measured microscopically or can be calculated as in WO94/08627.

Preferably, at least 75%, 90%, 95%, 98.0%, 98.5% or 99% of the protein in any of the said three kinds of microspheres is sufficiently cross-linked to be resistant to extraction with a 1% HCl solution for 2 minutes. Extracted protein is detected using the Coomassie Blue protein assay, Bradford. The protein content in the washings is expressed as a percentage of the original mass of microcapsules. The degree of cross-linking is controlled as in WO 94/08627.

The large, long life or targeted hollow microspheres may be such that at least 10% of the microspheres, when suspended in water, are capable of surviving a 0.25 s application of a pressure of $2.66 \times 10^4$ Pa without bursting, collapsing or filling with water. The transient maximum pressure in the human left ventricle is about 200 mm Hg ($2.66 \times 10^4$ Pa). Preferably 50%, 75%, 90% or 100% survive the said 0.25 s application of $2.66 \times 10^4$ Pa when tested as above, ie remain echogenic. In vivo, preferably the same percentages will remain echogenic during one passage through both ventricles of the heart.

The "large" microspheres may be characterised by the fact that at least 90%, preferably at least 95% or 99%, of the microspheres have a diameter within the range 10.1–19.9 μm, preferably 13–18 μm.

It should be noted that these microspheres are "large" only in relation to the preferred microspheres of WO 92/18164 and in relation to the preferred sizes of long life and targeted microspheres disclosed herein; prior art microspheres were frequently larger than 25 μm.

The large microspheres may be produced by controlling the parameters of the spray-drying process, as in WO 94/08627.

The large microspheres are suitable for use as a deposit echocontrast agent to delineate under-perfused areas of microcirculation. We have found that microspheres of mean size 12.0 to 15.0 μm have echogenicities some $4.6 \times 10^4$ fold higher than similar microspheres of mean size 5.0 μm. Hence, a relatively low dose can be used to image regions deep inside the body which are inaccessible to normal ultrasound techniques. A typical population of such large microspheres would have a mean size of 12.0 μm and 85% lying in the diameter range 9.0–18.0 μm.

Due to the pressure stability of the preferred microspheres, they retain air and hence echogenicity for a substantial period of time. The microspheres may deposit in the vasculature following catheter administration in a manner similar to classical microsphere studies, reflecting the amount of flow to any given perfusion territory. Imaging of the territory may then be made after catheter withdrawal and patient stabilisation, to enable more optimal images in multiple planes to be gathered. Comparison with a baseline unenhanced image thus enables the perfusion, following a corrective procedure, to be assessed.

The microspheres may be tailored for intracoronary use not only by manipulation of their size and pressure stability but also by their rate of biodegradation.

For intracoronary use, it is preferable to crosslink the large (10–20 μm) microcapsules at 175° C. for a period of 18–60 minutes, more preferably 20–40 minutes and most preferably 35–40 minutes. This yields microcapsules that are pressure resistant but have a shortened tissue half life compared to the microcapsules of WO 92/18164 and therefore are more applicable to use in the microcirculation of the myocardium. The tissue half-life can be measured by labelling the microcapsules with $^{125}$I by the Chloramine T method and assessing the organ content of microcapsules by necropsy or the release of $^{125}$I into the urine and faeces.

The "targeted" microspheres of the invention are characterised by having in or on their walls a material to direct or target the microspheres to a desired location in the body.

The "targeted" microspheres of the invention may be prepared by including in or on the wall of the microsphere material which alters the electrical charge of the microsphere.

Thus, a positive or negative charge can be imparted by applying a positively or negatively charged material, respectively, or existing positive or negative charges can be reduced or eliminated, as in WO 94/08627.

The "long-life" microspheres have an increased circulation time in the body, such that serum $t_{1/2}$ is at least 5 minutes, preferably at least 10 minutes and most preferably at least 15 minutes. Such increased circulation times may be achieved by coating the microspheres with a material which directs the microspheres away from the reticulo-endothelial system.

For example, the said material may be one which reduces or substantially prevents "opsonization", the deposition of proteinaceous material (such as fibrinogen) on the microspheres, thus directing the microspheres away from the liver and spleen. Suitable materials with which to coat the microspheres include block copolymers of the poloxamer series (ie polyethylene glycol/polyethylene oxide copolymers), such as poloxamer 338, poloxamer 407 and poloxamer 908.

The long-life microspheres are prepared in the same way as the targeted microspheres described above, in other words the coating material may be applied to a suspension of the spray-dried microspheres before they are freeze-dried or included in the spray feedstock, as in WO 94/08627.

Preferably, the microcapsules are made by the method of WO 96/15814. That is to say, the process comprises (i) providing a solution of an aqueously-soluble material in an aqueous solvent and (ii) spraying the said solution into a gas such that the aqueous solvent evaporates, thereby forming hollow microcapsules, wherein in that the aqueous solution contains a liquid of greater volatility than water.

Suitable volatile liquids include ethanol (the preferred volatile liquid) (boiling point 78.3° C.), methanol (b.p. 64.5° C.), and acetone (b.p. 56° C.). The volatile liquid needs to act as a solvent for the wall-forming material and be miscible with water at the ratios used.

The proportion of the aqueous solution which is the volatile liquid will vary according to the identity of the volatile compound, the concentration and identity of the wall-forming material, the temperature and pressures at which the solution is to be sprayed, and the microcapsule product desired. Typically, between 0.1% and 80% v/v, preferably 1–50% v/v and most preferably 5–30% v/v, for example about 20% v/v, of the solution is the volatile liquid. Mixtures of volatile liquids may be used, in which case these percentages refer to the total content of volatile liquid.

The spray-drying may be a one step process such as to provide the desired microcapsule product immediately. Alternatively, the immediate product may be subjected to further process steps, for example heating to further crosslink and insolubilise the protein shell of the microcapsules. This constitutes a two step process.

For a product which is to be injected into the human bloodstream, for example as an echogenic contrast agent in ultrasound diagnostic procedures (which is one intended use of the product), the total process is preferably carried out under sterile conditions. Thus, the protein solution is sterile and non-pyrogenic, the gas in the chamber is first passed through a 0.2 μm filter, the spray-drier is initially autoclaved and so on. Alternatively, or as well, the final product may be sterilised, for example by exposure to ionising radiation.

The wall-forming material is a water-soluble material, preferably a protein (the term being used to include non-naturally occurring polypeptides and polyamino acids). For example, it may be collagen, gelatin or (serum) albumin, in each case (if the microcapsules are to be administered to humans) preferably of human origin (ie derived from humans or corresponding in structure to the human protein) or polylysine or polyglutamate. It may be human serum albumin (HA) derived from blood donations or from the fermentation of microorganisms (including cell lines) which have been transformed or transfected to express HA. Alternatively, simple or complex carbohydrates, simple amino acids or fatty acids can be used, for example lysine, mannitol, dextran, palmitic acid or behenic acid.

Techniques for expressing HA (which term includes analogues and fragments of human albumin, for example those of EP-A-322094, and polymers of monomeric albumin) are disclosed in, for example, EP-A-201239 and EP-A-286424.

The aqueous solution or dispersion is preferably 0.1 to 50% w/v, more preferably about 1.0–25.0% w/v or 5.0–30.0% w/v protein, particularly when the material is albumin. About 5–15% w/v is optimal. Mixtures of wall-forming materials may be used, in which case the percentages in the last two sentences refer to the total content of wall-forming material.

The preparation to be sprayed may contain substances other than the wall-forming material, water and volatile liquid, and functional agents may be included, as in WO96/15814.

Similar aqueous phases can be used as the carrier liquid in which the final microcapsule product is suspended before use. Surfactants may be used (0.1–5% by weight) including most physiologically acceptable surfactants, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Other surfactants include free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids, glycerides or soya-oil and sucrose. Preferably, however, the carrier liquid does not contain a surfactant.

The solution of the wall-forming material is atomised and spray-dried by any suitable technique which results in discrete microcapsules of 0.05–50.0 μm diameter. These figures refer to at least 90% of the volume of microcapsules, the diameter being measured with a Coulter Multisizer II. The term "microcapsules" means hollow particles enclosing a space, which space is filled with a gas or vapour but not with any solid materials. Honeycombed particles resembling the confectionery sold in the UK as "Maltesers™" are not formed. It is not necessary for the space to be totally enclosed (although this is preferred) and it is not necessary for the microcapsules to be precisely spherical, although they are generally spherical. If the microcapsules are not spherical, then the diameters referred to above relate to the diameter of a corresponding spherical microcapsule having the same mass and enclosing the same volume of hollow space as the non-spherical microcapsule.

The atomising comprises forming an aerosol of the preparation by, for example, forcing the preparation through at least one orifice under pressure into, or by using a centrifugal atomizer in a chamber of warm air or other inert gas. The chamber should be big enough for the largest ejected drops not to strike the walls before drying. If the microcapsules are intended to be injected into the bloodstream for diagnostic imaging, then the gas or vapour in the chamber is clean (ie preferably sterile and pyrogen-free) and non-toxic when administered into the bloodstream in the amounts concomitant with administration of the microcapsules in echocardiography. The rate of evaporation of the liquid from the protein preparation should be sufficiently high to form hollow microcapsules but not so high as to burst the microcapsules. The rate of evaporation may be controlled by varying the gas flow rate, concentration of protein in the protein preparation, nature of liquid carrier, feed rate of the solution and, most importantly, the temperature of the gas encountered by the aerosol. Small size distributions are achieved by spray-drying in which there is a combination of low feed stock flow rate with very high levels of atomisation and drying air. The effect is to produce microcapsules of very defined size and tight size distribution. Several workers have designed equations to define the mean droplet size of pneumatic nozzles; a simple version of the various parameters which affect mean droplet size is given in WO 96/15814.

With an albumin concentration of 5.0–25.0% in water, an inlet gas temperature of at least about 100° C., preferably at least 110° C., is generally sufficient to ensure hollowness and the temperature may be as high as 250° C. without the capsules bursting. About 180–240° C., preferably about 210–230° C. and most preferably about 220° C., is optimal, at least for albumin. The temperature may, in the one step version of the process of the invention, be sufficient to insolubilise at least part (usually the outside) of the wall-forming material and frequently substantially all of the wall-forming material. Since the temperature of the gas encountered by the aerosol will depend also on the rate at which the aerosol is delivered and on the liquid content of the protein preparation, the outlet temperature may be monitored to ensure an adequate temperature in the chamber. An outlet temperature of 40–150° C. has been found to be suitable.

In the two step process, if the wall-forming material is a protein, the intermediate microcapsules comprise typically 96–98% monomeric protein and retain the same water solubility as the wall-forming material itself. They have a limited in vivo life time for ultrasound imaging. They may, however, be used for ultrasound imaging, or they may be stored and transported before the second step of the two step process is carried out. They therefore form a further aspect of the invention.

In the second step of the process, the intermediate microcapsules prepared in the first step are fixed and rendered less water-soluble, as on WO96/15814, so that they persist for longer whilst not being so insoluble and inert that they are not biodegradable. This step also strengthens the microcapsules so that they are better able to withstand the rigours of administration, vascular shear and ventricular pressure.

The final product, measured in the same way as the intermediate microcapsules, may, if one wishes, consist of microcapsules having a diameter of 0.1 to 50.0 μm, but volume ranges of 0.1 to 20.0 μm and especially 1.0 to 8.0 μm are obtainable with the process of the invention and are preferred for echocardiography. One needs to take into account the fact that the second step may alter the size of the microcapsules in determining the size produced in the first step.

In particular, a product having a high degree of reflectivity, relative to the amount of wall-forming material, may be obtained. For example, a homogeneous suspension of 13 μg/ml of microcapsules can provide a reflectivity to 3.5 MHz ultrasound of at least −1.0 dB. Higher reflectivities than −0.3 may be unnecessary, and a reflectivity of around −0.7 to −0.5 is convenient.

The microcapsules can be stored dry in the presence or in the absence of additives to improve conservation, prevent coalescence or aid resuspension. As additives, one may select from 0.1 to 200.0% by weight of water-soluble physiologically acceptable compounds such as mannitol, galactose, lactose or sucrose or hydrophilic polymers like dextran, xanthan, agar, starch, PVP, polyglutamic acid, polyvinylalcohol (PVA) and gelatin.

Any agglomeration of the microcapsules can be minimised by the methods taught in WO 96/15814.

Preferably, the steps of resuspending the product and then freeze-drying the suspension, which are options in WO 96/15814, are not performed. The microcapsules are simply milled with any desired additives (eg lactose) and filled into final containers.

The product is hence generally supplied and stored as a dry powder and is suspended in a suitable sterile, non-pyrogenic liquid just before administration. The suspension is generally administered by injection of about 0.05 to 5.0 ml into a suitable vein such as the cubital vein or other bloodvessel. A microcapsule concentration of about $1.0\times10^5$ to $1.0\times10^{12}$ particles/ml is suitable, preferably about $5.0\times10^5$ to $5.0\times10^9$. The number of microcapsules administered can therefore be from $5.0\times10^3$ to $5.0\times10^{12}$.

Low frequency echocontrast imaging of microcapsules according to the invention can be utilised to image all organs/vessels in the body including perfusion imaging of the liver, which is useful in screening for cancers etc.

Although ultrasonic imaging is applicable to various animal and human body organ systems, one of its main applications is in obtaining images of myocardial tissue and perfusion or blood flow patterns.

The techniques use ultrasonic scanning equipment consisting of a scanner and imaging apparatus. The equipment produces visual images of a predetermined area, for example the heart region of a human body. Typically, the transducer is placed directly on the skin over the area to be imaged. The scanner houses various electronic components including ultrasonic transducers. The transducer produces ultrasonic waves which perform a sector scan of the heart region. The ultrasonic waves are reflected by the various portions of the heart region and are received by the receiving transducer and processed in accordance with pulse-echo methods known in the art. After processing, signals are sent to the imaging apparatus (also well known in the art) for viewing.

For commercially available machines which have more than one ultrasound probe fitted, better echocontrast images will be obtained with microcapsules of the invention by using the lower frequency probe. For example, Advanced Technology Laboratories (ATL) HDI 3000, Ultrasound Machine: P3-2 probe generates better images than the P5-3 probe (harmonic imaging and fundamental imaging).

The improvement of echocontrast imaging with microcapsules at lower frequency according to the invention is seen both in fundamental and harmonic mode, with and without intermittent imaging.

In the method of the present invention, after the patient is "prepped" and the scanner is in place, the microcapsule suspension is injected, for example through an arm vein. The contrast agent flows through the vein to the right venous side of the heart, through the main pulmonary artery leading to the lungs, across the lungs, through the capillaries, into the pulmonary vein and finally into the left atrium and the left ventricular cavity of the heart.

With these microcapsules, observations and diagnoses can be made with respect to the amount of time required for the blood to pass through the lungs, blood flow patterns, the size of the left atrium, the competence of the mitral valve (which separates the left atrium and left ventricle), chamber dimensions in the left ventricular cavity and wall motion abnormalities. Upon ejection of the contrast agent from the left ventricle, the competence of the aortic valve also may be analyzed, as well as the ejection fraction or percentage of volume ejected from the left ventricle. Finally, the contrast patterns in the tissue will indicate which areas, if any, are not being adequately perfused.

In summary, such a pattern of images will help diagnose unusual blood flow characteristics within the heart, valvular competence, chamber sizes and wall motion, and will provide a potential indicator of myocardial perfusion.

The microcapsules may permit left heart imaging from intravenous injections. The albumin microcapsules, when injected into a peripheral vein, may be capable of transpulmonary passage. This results in echocardiographic opacification of the left ventricle (LV) cavity as well as myocardial tissue.

Besides the scanner briefly described above, there exist other ultrasonic scanners, examples of which are disclosed in U.S. Pat. Nos. 4,134,554 and 4,315,435. Basically, these patents relate to various techniques including dynamic cross-sectional echography (DCE) for producing sequential two-dimensional images of cross-sectional slices of animal or human anatomy by means of ultrasound energy at a frame rate sufficient to enable dynamic visualisation of moving organs. Types of apparatus utilised in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable devices in a manner somewhat analogous to radar or sonar displays. While DCE can be used to produce images of many organ systems including the liver, gall bladder, pancreas and kidney, it is frequently used for visualisation of tissue and major blood vessels of the heart.

The microcapsules may be used for imaging a wide variety of areas, even when injected at a peripheral venous site. Those areas include (without limitation): (1) the venous drainage system to the heart; (2) the myocardial tissue and perfusion characteristics during an exercise treadmill test or the like; and (3) myocardial tissue after an oral ingestion or intravenous injection of drugs designed to increase blood flow to the tissue. Additionally, the microcapsules may be useful in delineating changes in the myocardial tissue perfusion due to interventions such as (1) coronary artery vein grafting; (2) coronary artery angioplasty (balloon dilation of a narrowed artery); (3) use of thrombolytic agents (such as streptokinase) to dissolve clots in coronary arteries; or (4) perfusion defects or changes due to a recent heart attack.

Furthermore, at the time of a coronary angiogram (or a digital subtraction angiogram) an injection of the microcapsules may provide data with respect to tissue perfusion characteristics that would augment and complement the data obtained from the angiogram procedure, which identifies only the anatomy of the blood vessels.

Through the use of the microcapsules of the present invention, other non-cardiac organ systems including the liver, spleen and kidney that are presently imaged by ultrasonic techniques may be suitable for enhancement of such currently obtainable images, and/or the generation of new images showing perfusion and flow characteristics that had not previously been susceptible to imaging using prior art ultrasonic imaging techniques.

Non-body imaging can also be performed, for example in plastic pipes to reveal obstructions.

EXAMPLE 1

A suitable spray dryer is available from A/S Niro Atomizer, Soeborg, Denmark under the trade designation "Mobile Minor".

A 10.0% w/v solution of sterile, pyrogen-free rHA in pyrogen-free water (suitable for injection) with 25.0% v/v ethanol was pumped to the nozzle of a two fluid nozzle atomiser mounted in the commercial spray drying unit described above. The peristaltic pump speed was maintained at a rate of approximately 4.0 g/minute such that with an inlet air temperature of 220° C. the outlet air temperature was maintained at 95° C.

Compressed air was supplied to the two fluid atomising nozzle at 2.0–10.0 Bar ($2.0$–$6.0 \times 10^5$ Pa). In this range microcapsules with a mean size of 2.0–3.0 µm are obtained.

Typically an increase in mean particle size (by reduced atomisation pressure) led to an increase in the amount of microcapsules over 10 µm in size (see Table 1).

TABLE 1

Effects of atomisation pressure on frequency of microcapsules over 10 µm in diameter

| Atomisation Pressure ($\times 10^5$ Pa) | % Frequency over 10 µm |
| --- | --- |
| 6.0 | 0.8 |
| 5.0 | 3.0 |
| 3.5 | 6.6 |
| 2.5 | 8.6 |
| 2.0 | 13.1 |

A pressure of $5.0 \times 10^5$ Pa was used to generate the microcapsules in this specific example.

In the second step of the process, 5 g of microcapsules were heated in a glass beaker using a Gallenkamp fan oven. A temperature of 175° C. for 1 hour was sufficient to yield microcapsules with 100% fixation as determined by HPLC. The effect of this heat fixation was to increase the in vitro echogenic half life from a few seconds to in excess of 30 minutes. By altering the temperature and length of incubation it is possible to vary the degree of fixation between about 5% and 100%.

Following heat fixation, the microcapsules were deagglomerated and dispersed into water in one of two ways. Method 1 involved first mixing the heat fixed spheres with an equal weight of finely milled lactose (mean diameter 5 μm). The mixture was then passed through a Fritsch centrifugal mill with a 0.5 mm screen and 12 tooth rotor. The milled spheres were collected and passed through the mill a second time to ensure complete mixing had occurred. The milled powder was then resuspended in water containing 1 mg.ml$^{-1}$ Pluronic F68™. Typically 10 g of microcapsules and lactose was added to 100 ml of water and Pluronic F68. Method 2 for deagglomeration involves adding 5 g of the heat-fixed microcapsules to 100 ml of water containing 100 mg of Pluronic F68. The microcapsules were dispersed using a Silverson homogeniser (model L4R with a 2.54 cm tubular homogenising probe and a high shear screen) and homogenising for 60 seconds.

The resuspended spheres were separated into intact (gas containing) and broken spheres using a flotation technique. The gas-containing spheres were seen to float to the surface over a 1 hour period and were decanted from the sinking fraction which does not contain the gas required.

The separation process can be accelerated by centrifugation. A 30 second centrifugation at 5000×g is sufficient to separate the two fractions.

Following separation the intact microcapsules were freeze-dried in the presence of lactose and Pluronic F68. Optimal conditions for freeze drying involved resuspending 30 mg of microcapsules in 5 ml of water containing 50 mg of lactose and 5 mg of Pluronic F68. The freeze-dried microcapsules can be redispersed in a liquid (eg water, saline) to give a monodisperse distribution.

EXAMPLE 2

Microcapsules were prepared as in Example 1 but under the conditions detailed below.

A 100±10 mg/ml solution of sterile, pyrogen-free serum-derived human albumin in pyrogen-free water (suitable for injection) with 25% w/w ethanol was used as the spray drying feedstock.

Using a peristaltic pump, the albumin feedstock was pumped at a rate of 4±1.5 g/min such that, with an inlet temperature of 220±0.5° C., an outlet temperature of 80±10° C. was maintained.

Additional spray-drying conditions were as follows: air flow, 50±2%; atomization pressure, 8.0±0.5 barg; drying air flow, 9±2 mm H$_2$O.

The microcapsules produced were heat-fixed at a temperature of 176±2° C. for 55±5 min in 5±1 g aliquots in 250 ml stainless steel beakers.

Following heat-fixation, the microcapsules were deagglomerated. Glucose was added to the pooled microcapsules at a ratio of 2:1, mixed and milled with a Glen Creston air impact jet mill.

The deagglomerated microcapsules were filled into glass vials, and the vials purged with nitrogen, sealed and capped. The product was terminally sterilised by irradiating at a dose of between 25–35 kGy.

EXAMPLE 3

Optimisation of Spray Drying Conditions to Maximise the Number of Intact Gas-Containing Particles We describe above the production of smooth, spherical and hollow microparticles for use in echocontrast imaging. It is desirable to minimise the number of particles larger than 6 μm and to maximise the number of gas-containing hollow particles. A series of experiments were performed under the conditions described in Example 1 to examine the influence of liquid feed rate on the yield of intact spherical particles. We found that increasing the liquid feed rate decreased the number of intact microparticles formed during the initial spray drying (Table 2). The mean particle size and overall pressure stability, ie thickness of the shell, do not change but the total echogenicity does, as the liquid flow rate is increased from 4 to 16 ml/min. We find that slower rates of evaporation (at higher liquid flow rates) lead to fewer intact gas-containing particles being formed.

TABLE 2

| | Flow rates (ml/min) | | | |
|---|---|---|---|---|
| | 4 | 8 | 12 | 16 |
| Mean size (μm) | 3.08 | 3.04 | 3.13 | 3.07 |
| Echogenicity (video density units) | 22 | 21 | 14 | 10 |
| Echogenicity after pressure (video density units) | 20 | 18 | 10 | 8 |

EXAMPLE 4

Hyaluronic acid at a concentration of 5% w/v was incubated overnight with resuspended microspheres prepared as in Example 1 at 20° C. (100×10$^6$ microspheres/ml). Mannitol and Pluronic F68 were added to a concentration of 10 and 0.06 mg/ml respectively and the suspension then flash frozen and freeze dried.

EXAMPLE 5

Microspheres according to Example 1 were resuspended in a solution of DMF (dimethylformamide) at a concentration of 100×10$^6$ particles/ml. Acetic anhydride was added to give a final acid anhydride concentration of 100 mg/ml. The microsphere mixture was incubated at 20° C. for 1 hour, then diluted with water and filtered washed with excess water over a one hour period. The microspheres were formulated in mannitol and Pluronic F68 as described above. This method imparts negative charges.

EXAMPLE 6

Myocardial Perfusion Imaging

A beneficial use of the improved contrast imaging at low frequency afforded by the invention is in the determination of myocardial perfusion. This is an important parameter in determining the precise risk areas, infarcts and ischemic regions in the heart.

Method

A 35 kg open-chested dog was prepared and baseline (pre-contrast) images obtained of the heart using the ATL HDI 3000 ultrasound machine at a Mechanical Index (MI) power setting of 0.4 (machine has range of from 0.4–0.8). Images were collected using intermittent imaging triggered by electrocardiograph (ECG) wave and P3-2 (3.2 MHz) probe in harmonic mode.

Following baseline imaging, 0.8 cc of the microcapsules was injected into the venous circulation and the heart imaged without altering the baseline settings.

Comparison of the pre-dose and the post-dose image revealed that myocardial perfusion could be detected in the heart after administration of the microcapsules.

A repeat injection of microcapsules was made approximately 30 minutes after the first microcapsule dose, but, imaging was performed by the higher frequency probe (P5-3=5.3 MHz).

Significantly less echocontrast was observed (above baseline) with the higher frequency probe.

In subsequent studies the presence of selected coronary artery occlusions, perfusion defects could be better delineated at lower frequencies using the method of the invention.

EXAMPLE 7

Liver Perfusion Imaging

The use of contrast imaging to determine liver perfusion is an extremely useful technique in evaluating the presence and extent of liver cancer/metastasis.
Method A 35 kg close chested dog was anaesthetized and presented for imaging. The liver of the dog was imaged at baseline (pre-injection) using the ATL HDI 3000 machine. The lower frequency P3-2 probe was used to image the liver in the harmonic intermittent mode.

Following baseline imaging, 5.0 cc of the microcapsules was administered to the dog and imaging of the liver recommenced without adjusting. Excellent perfusion images were obtained with the microcapsules of the invention. The images were significantly better than those obtained at higher (P5-3) frequencies.

EXAMPLE 8

Imaging at Very Low Frequencies

Whilst other imaging agents give poor images at lower frequencies, the microcapsules of the invention will generate improved images. For example, at very low frequencies (2.25 MHz or less, preferably <1.8 MHz) clinically useful echocontrast perfusion images can be generated.
Method A 35 kg close-chested dog was prepared as in Example 7.

An experimental 1.0 MHz probe was connected to a Hewlett-Packard HP2500 ultrasound imaging machine. The dog heart was then imaged in both fundamental and harmonic mode using both real time and triggered imaging.

Following the intravenous (IV) administration of 0.5 cc of the microcapsules, excellent myocardial perfusion images can be generated over prolonged periods, for example, greater than 5 minutes.

What we claim is:

1. A method of generating an ultrasound image comprising the steps of (i) introducing into a location to be imaged an ultrasound contrast agent obtained by spraying a solution or suspension of a wall forming material into a heated gas to form hollow microcapsules, (ii) exposing the microcapsules to ultrasound energy at an insonation frequency of less than 3.5 MHz and (iii) creating an image based on the scattering of the ultrasound energy caused by the microcapsules.

2. A method of generating an ultrasound image comprising the steps of (i) introducing into a location to be imaged an ultrasound contrast agent obtained by spraying a solution or suspension of a wall forming material into a heated gas to form hollow microcapsules, (ii) exposing the microcapsules to ultrasound energy, the insonation frequency being varied below 3.5 MHz in order to identify and use a frequency at which the ultrasound is scattered optimally by the microcapsules, and (iii) creating an image based on the scattering of the ultrasound energy caused by the microcapsules.

3. A method as claimed in claim 1 or 2 wherein the insonation frequency is less than 2.25 MHz.

4. A method as claimed in claim 3 wherein the insonation frequency is from 2.0 to 1.0 MHz.

5. A method as claimed in claim 1 or 2 wherein the ultrasound energy exposed to the microcapsules in step (ii) has an acoustic peak pressure amplitude of at least 100 kPa.

6. A method according to any one of claims 1 to 2 wherein the microcapsules are obtained by spraying as said an aqueous solution of a water-soluble wall-forming material containing a liquid of a volatility greater than that of water.

7. A method according to any one of claims 1 to 2 wherein the microcapsules are not freeze-dried.

8. A method according to any one of claims 1 to 2 wherein the microcapsules have a diameter of 0.1 to 25.0 μm.

9. A method according to any one of claims 1 to 2 wherein the said location is within the human or animal body.

10. A method as claimed in claim 9 wherein the said location is an internal organ.

11. A method according to claim 10 wherein the internal organ is the human or animal heart.

12. A method according to claim 10 wherein the internal organ is the human or animal liver.

* * * * *